United States Patent
Patel et al.

(10) Patent No.: US 10,593,145 B2
(45) Date of Patent: Mar. 17, 2020

(54) SYSTEM AND METHOD FOR DISPENSING MEDICINE USING A MANUAL FILL TRAY APPARATUS

(71) Applicants: Miteshkumar Ishwarbhai Patel, San Leandro, CA (US); Raj Kalpesh Patel, San Jose, CA (US)

(72) Inventors: Miteshkumar Ishwarbhai Patel, San Leandro, CA (US); Raj Kalpesh Patel, San Jose, CA (US)

(73) Assignee: MEDITAB SOFTWARE, INC., Sacramento, CA (US)

( * ) Notice: Subject to any disclaimer, the term of this patent is extended or adjusted under 35 U.S.C. 154(b) by 182 days.

(21) Appl. No.: 15/710,819

(22) Filed: Sep. 20, 2017

(65) Prior Publication Data
US 2019/0088070 A1    Mar. 21, 2019

(51) Int. Cl.
*G07F 17/00*    (2006.01)
*A61J 1/03*    (2006.01)
(Continued)

(52) U.S. Cl.
CPC .......... *G07F 17/0092* (2013.01); *A61J 1/035* (2013.01); *A61J 7/0069* (2013.01);
(Continued)

(58) Field of Classification Search
CPC ...... G07F 17/0092; G07F 11/00; G07F 11/62; A61J 1/035; A61J 7/0069; A61J 7/04; A61J 2205/60; G16H 20/13
(Continued)

(56) References Cited

U.S. PATENT DOCUMENTS

| 4,763,810 A * | 8/1988 | Christiansen | A61J 7/04 |
| | | | 221/15 |
| 6,581,356 B2 * | 6/2003 | Kim | B65B 5/103 |
| | | | 221/119 |

(Continued)

*Primary Examiner* — Michael Collins
(74) *Attorney, Agent, or Firm* — Firasat Ali; Creso Legal LLP

(57) ABSTRACT

Systems and methods are disclosed for a medical pill dispensing system using a manual fill tray. The system includes a plurality of canisters and/or a manual fill trays for storing one or more pills. Each of the plurality of canisters and/or manual fill trays are configured to dispense one or more pills that are to be packed for a patient. The system also includes a hopper system that receives the pills dispensed from either a canister and/or a manual fill tray.

The manual fill tray includes a plurality of storage section. Each storage section includes a plurality of slots that are open to its top and bottom. Each storage section includes its own dispensing belt which wraps around the slots of the storage section. The wrapping creates a base at the bottom of each slot as well as either an opening or a cover for the top of each slot. The dispensing belt includes dispensing openings and deposition openings.

The system operates the manual fill tray in one of three modes, depositing mode, lockdown mode, and dispensing mode. In its deposition mode, an RFID system coupled to the manual fill tray reads an RFID tag on a container that is used for depositing pills into the slots of the manual fill tray. The system queries a database to verify that the pills in the depositing container are meant for the specific patient for whom the system is currently processing a pill package. Upon confirmation, system authorizes deposition of pills and displaces the dispensing belt such that its deposition openings overlap the slots of the manual fill tray thereby creating an opening to the top and allowing deposition while (Continued)

at the same time ensuring that the bottom of the dispensing belt acts as a base to the slots to hold the pills deposited therein.

In its lockdown mode, the system displaces the dispensing belt such that both the top and bottom of the slots are covered by the dispensing belt thereby not allowing any deposition or dispensing from the slots. In its lockdown mode, the system displaces the dispensing belt such that In its lockdown mode, the system displaces the dispensing belt such that the dispensing opening of the dispensing belt is moved under a desired slot to allow pills from that slot to be dispensed into a receptacle, such as a hopper. The dispensing follows a logic that allows the sequential in-line dispensing from one slot to the next in a single row. A feedback and confirmation system is used to determine if the pills dropped from the first pill slot have cleared the receptacle, such as the hopper, and upon confirmation the pills from the second slot are dispensed.

The dispensed pills navigate through various compartments of the system and ultimately to a pill pack where they are packaged for a specific patient.

16 Claims, 13 Drawing Sheets

(51) Int. Cl.
| | | |
|---|---|---|
| *G06F 17/00* | (2019.01) | |
| *G06F 19/00* | (2018.01) | |
| *A61J 7/00* | (2006.01) | |
| *G07F 11/60* | (2006.01) | |
| *G07F 11/62* | (2006.01) | |
| *G16H 20/13* | (2018.01) | |
| *G06Q 50/22* | (2018.01) | |
| *A61J 7/04* | (2006.01) | |
| *G16H 10/60* | (2018.01) | |

(52) U.S. Cl.
CPC .......... *G06F 19/3462* (2013.01); *G07F 11/60* (2013.01); *G07F 11/62* (2013.01); *G16H 20/13* (2018.01); *A61J 7/04* (2013.01); *A61J 2205/60* (2013.01); *G06Q 50/22* (2013.01); *G16H 10/60* (2018.01)

(58) Field of Classification Search
USPC .................................................. 700/231–244
See application file for complete search history.

(56) References Cited

U.S. PATENT DOCUMENTS

| | | | | |
|---|---|---|---|---|
| 7,726,095 | B2* | 6/2010 | Yuyama | B65B 5/103 221/253 |
| 8,103,379 | B2* | 1/2012 | Biba | G07F 11/18 700/243 |
| 2004/0134043 | A1* | 7/2004 | Uema | G07F 11/62 24/297 |
| 2005/0145644 | A1* | 7/2005 | Mori | B65B 5/103 221/242 |
| 2015/0066204 | A1* | 3/2015 | Patel | G06F 19/3462 700/232 |

* cited by examiner

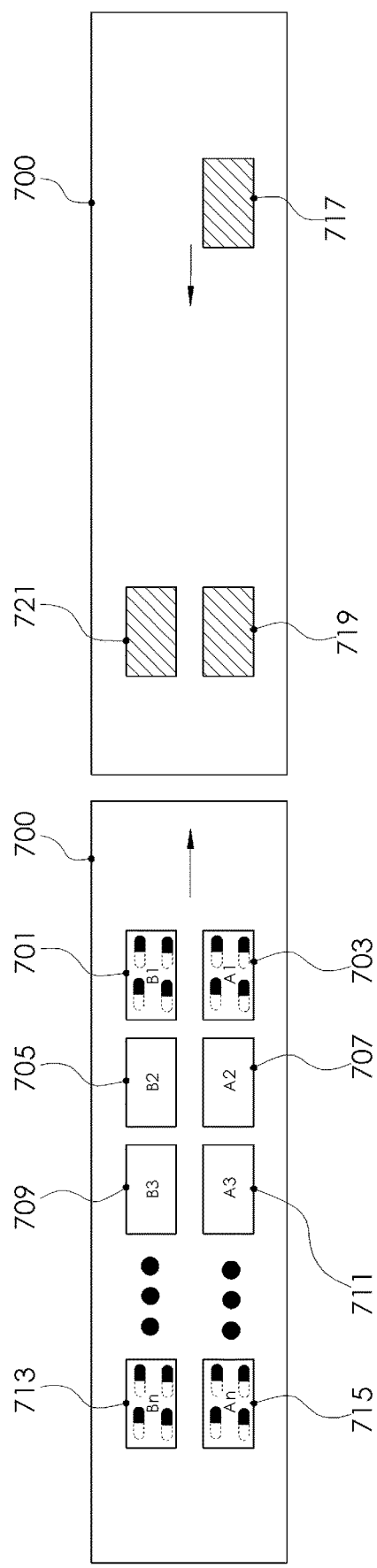
FIG. 7A
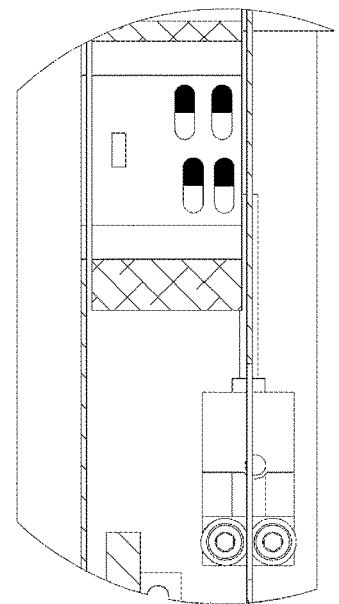
FIG. 7B
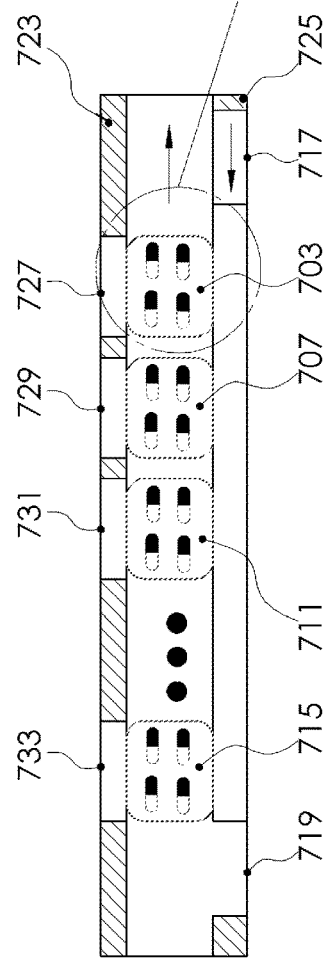
FIG. 7C
FIG. 7D

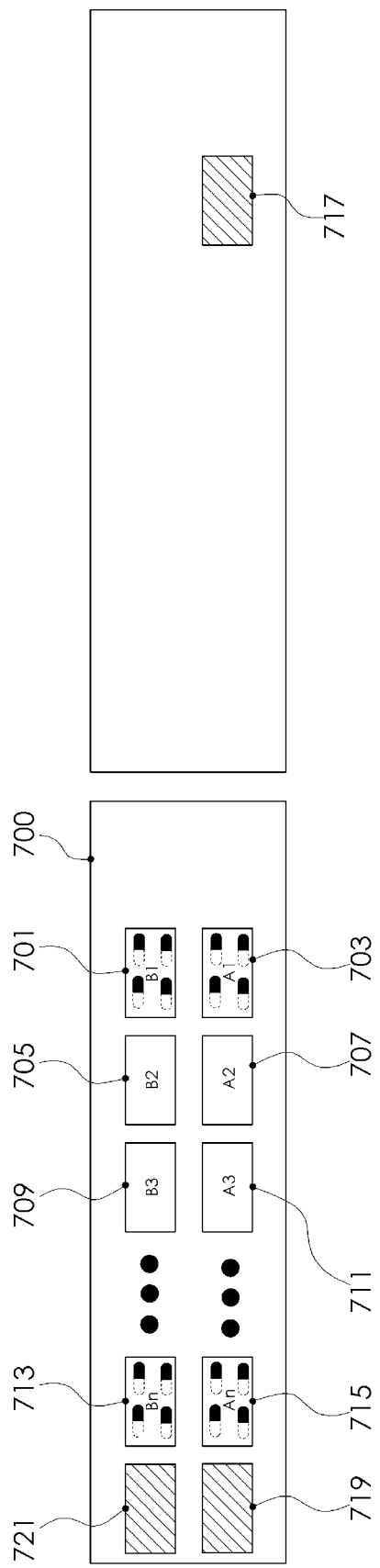
FIG. 8A
FIG. 8B
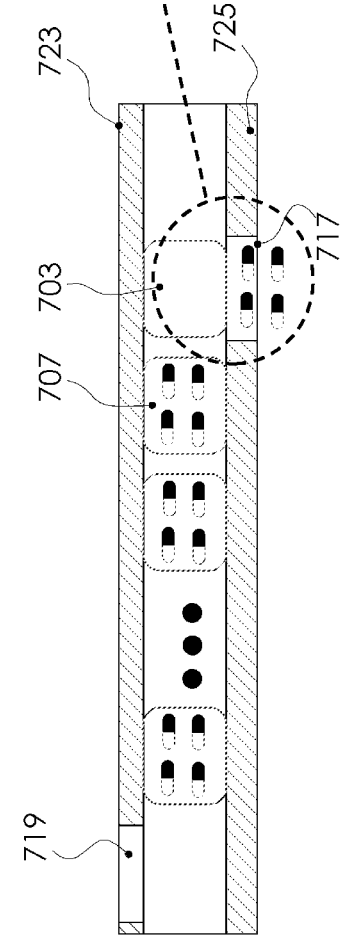
FIG. 8C
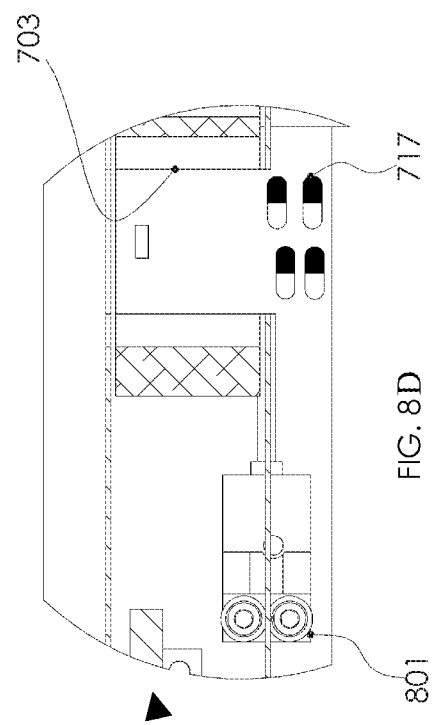
FIG. 8D

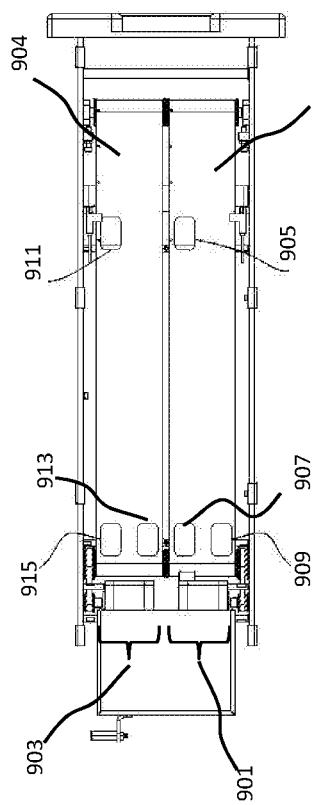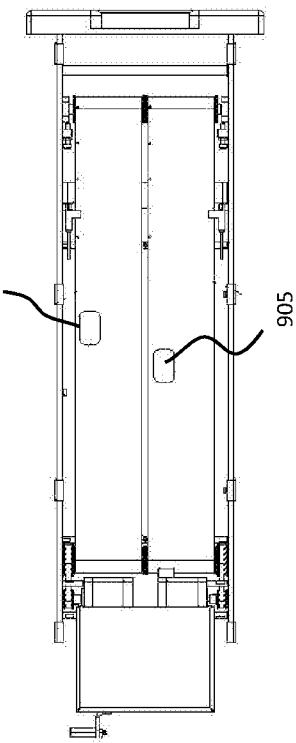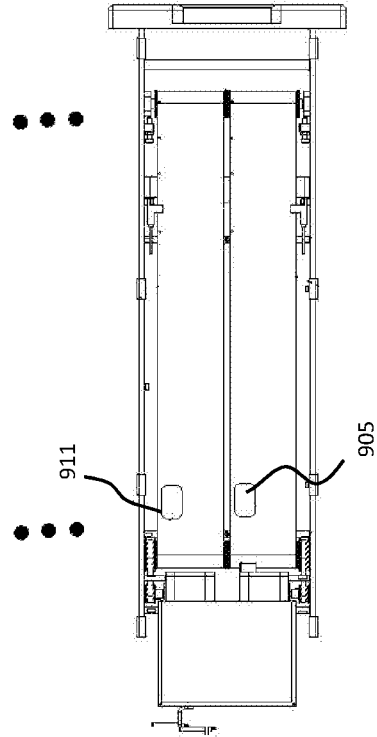

SYSTEM AND METHOD FOR DISPENSING MEDICINE USING A MANUAL FILL TRAY APPARATUS

CONTINUATION INFORMATION

This application is a continuation-in-part of an application Ser. No. 15/704,056, titled "MEDICAL DISPENSING SYSTEM WITH FEEDBACK PRE-FILL APPARATUS," filed on Sep. 14, 2017, having Miteshkumar Ishwarbhai Patel as an inventor. Application Ser. Nos. 15/704,056, and 14/155,873 are also incorporated herein by reference.

BACKGROUND OF THE INVENTION

Field of the Invention

This application is related to system and method for dispensing medicine, and more particularly, to using a manual fill tray apparatus.

Description of the Related Art

Manufacturing systems are used to dispense medicines and package them. These systems use storage units to house medicines and then dispense them into pill packages. Typically, these storage units are available in one standard size that can fit into the manufacturing system. Since the manufacturing systems are designed to package pill packs at a high volume, the storage systems that store the medication likewise store medications that are used in high volume.

One drawback of the existing system is that they are unable to accommodate medications that are required in small quantities. They are also unable to accommodate for specific drugs that are just needed for a handful or smaller volume of patients. Another drawback of these systems includes inefficient and cumbersome processing in handling a pill pack that requires a specific medication that is not stored by the storage system. Yet another drawback of the existing systems is the inability to anticipate the needs of specific low volume medications and verify their dispensing quantities.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

FIG. 7A depicts a top view of the pill dispensing belt in its initial position, according to some embodiments.

FIG. 7B depicts a bottom view of the pill dispensing belt in its initial position, according to some embodiments.

FIG. 7C depicts a side view of the pill dispensing belt in its initial position, according to some embodiments.

FIG. 7D is a detailed view of the pill dispensing belt in its initial position, according to some embodiments.

FIG. 8A depicts a top view of the pill dispensing belt in its initial dispensing position, according to some embodiments.

FIG. 8B depicts a bottom view of the pill dispensing belt in its initial dispensing position, according to some embodiments.

FIG. 8C depicts a side view of the pill dispensing belt in its dispensing position, according to some embodiments.

FIG. 8D is a detailed view of the pill dispensing belt in its dispensing position, according to some embodiments.

FIGS. 9A-9C are bottom views the pill dispensing belt during its various stages dispensing using a single opening, according to some embodiments.

Figure 1:
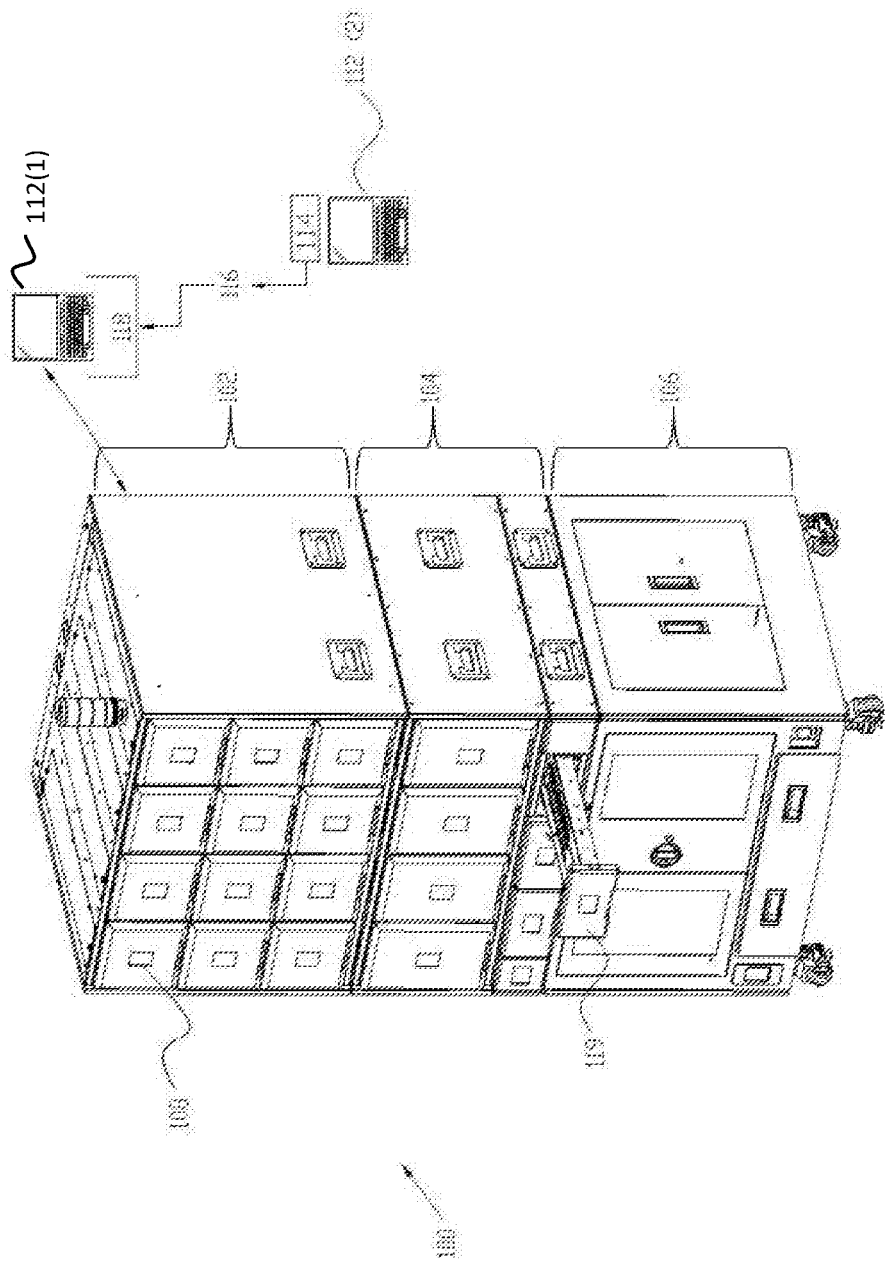
FIG. 1 is a block diagram of a general view of a pill dispensing robot that includes a manual fill tray, according to some embodiments.

While the embodiments of the application are susceptible to various modifications and alternative forms, specific embodiments are provided as examples in the drawings and detailed description. It should be understood that the drawings and detailed description are not intended to limit the embodiments to the particular form disclosed. Instead, the intention is to cover all modifications, equivalents and alternatives falling within the spirit and scope of the invention as defined by the appended claims.

DETAILED DESCRIPTION

The automated pill dispensing methods and systems described herein are directed to medical pill dispensers having a manual fill tray apparatus. The manual fill trays, as well as, other storage units, such as canisters, are part of an automated dispensing robot. The methods used by the systems include dispensing pills from the manual fill tray, and other storage units, such that the pills selectively make their way through various components of the robot and then ultimately get packaged in a pill pack designated for a specific patient. The dispensing by the manual fill tray and other storage units follows a prescription designated for a specific patient. The prescription and schedule of dispensing is stored in a database that communicates with the robot to dispense the type and quantity of pills required to be taken by the patient in accordance with their prescription plan. The manual fill tray, and its various features, allows storage of specific medications, such as medications that may be used in low quantities or medications that are uncommon, expensive, or need additional regulation or monitoring. Further the manual fill tray system also provides for additional verification to ensure that intended medications that are allocated for a specific patient are being dispensed by the manual fill tray into the pill packs thereby eliminating any incorrect dispensing errors.

FIG. 1 is a block diagram of a pill dispensing robot 100, according to one or more embodiments. Particularly, FIG. 1 depicts the outer body of the pill dispensing robot 100. The inner components, i.e. the machine body, which resides within the outer body, will be described in FIG. 2. The pill dispensing robot ("robot") 100 of FIG. 1 includes a canister drawer section 102, a manual fill tray section 104, and a dispensing section 106.

The canister drawer section 102, includes a plurality of canisters drawers 108 and a operation module (not shown). Each canister drawer 108 includes a plurality of canisters (204 shown in FIG. 2). Each canister 204 is designed to store medicines, i.e. pills, which are to be dispensed by the robot 100 in accordance with the prescription plan 116 for dispensing. The pills stored in each of the individual canisters may be of the same type. Each of the plurality of canisters may have a different types and sizes of pills thereby allowing the robot 100 to store several types of pills in the canister drawer section 102.

The manual fill tray section 104 includes a plurality of manual fill trays. These are fills trays that can be populated manually with medicines/pills by the operator of the robot 100. Each manual fill tray in this manual fill tray section 104 may be used to store a particular type of pill. These may be pills that are not commonly used by the robot. These may also be expensive pills that need close monitoring. These may be pills that require additional regulation, such as narcotics or morphine type of drugs that fall under the drug enforcement agency (DEA)'s stringent guidelines. Yet another type of pills category stored in the manual fill tray section are pills that are irregular in size and shape than the commonly used medications. Mostly, these may be drugs that are either infrequent to the high-volume operation of pill packing or require additional monitoring, control, or handling. In some cases, these may be medications that are not housed in the canisters; however, alternatively, an operator may choose to house the same type of medications as stored in the canisters in this section, i.e. the manual fill tray, as well.

The dispensing section 106 includes a hopper, a plurality of pre-fill trays, and a packing plate. The hopper is a component of the dispensing section 106 that goes from a wider opening at it top to a narrow opening bottom at it bottom thereby creating a funnel type apparatus. Each pre-fill tray, from the plurality of pre-fill trays, includes a grid of slots. The slots may be of a square shape. Alternatively, the slots may also be of rectangular or other shapes. The packing plate, or pack plate, is designed to accept a plurality of pill packs, also referred to as blister packs. A pill/blister pack is essentially the final pill pack that is used by a patient and includes the pills designated for the patient in accordance with the prescription plan. The packing plate slot is designed to accept a plurality of pill/blister packs. The packing plate locks the pill packs into their position such that they do not move with respect to the packing plate and allow for the dispensing of the pills into them.

Robot 100 also includes a computing device 122(1) for controlling robot 100 operations. Robot 100 can communicate with a computing device 122 (2) to receive plans for robot 100 operations. Computing device 122 (2) is configured to generate and/or modify plans for operation of robot 100.

Computing device 112 (1) and 112 (2) can be any type of a personal computer, a server, a mobile device, a personal assistant, and the like, including a device having memory for storing one or more applications and one or more processors.

In one embodiment, computing device 112 (1) and 112 (2) can be implemented using the same computing device.

Computing device 112 (2) can execute (e.g., by using the one or more processors) a plan generation module 116 to access, generate, and/or modify a plan 116. Plan 116 indicates a pill distribution by robot 100. Plan 116 is then communicated to a control module 118, which can be executed by computing device 112 (1) (e.g., by using one or more processors). Control module 118 processes the plan and controls the robot in accordance with the plan.

Dispensing section 106 is configured to receive pills from canisters (204 shown in FIG. 2) placed in the canister drawer 108 as well as manual fill trays that are in the manual fill tray section 104. The control module 118 allows selection of the pills associated with the prescription plan 116 from the respective canisters 204 and manual fill trays. The selected pills are then processed and dispensed, i.e., dropped, into the dispensing section 106. The pills make their way through the hopper and into a first pre-fill tray and then onto the second pre-fill tray and finally into the appropriate blister pack that is located in the packing plate.

Various embodiments of using such a control module and plan generation module are described with reference to the Figures below.

Figure 2:
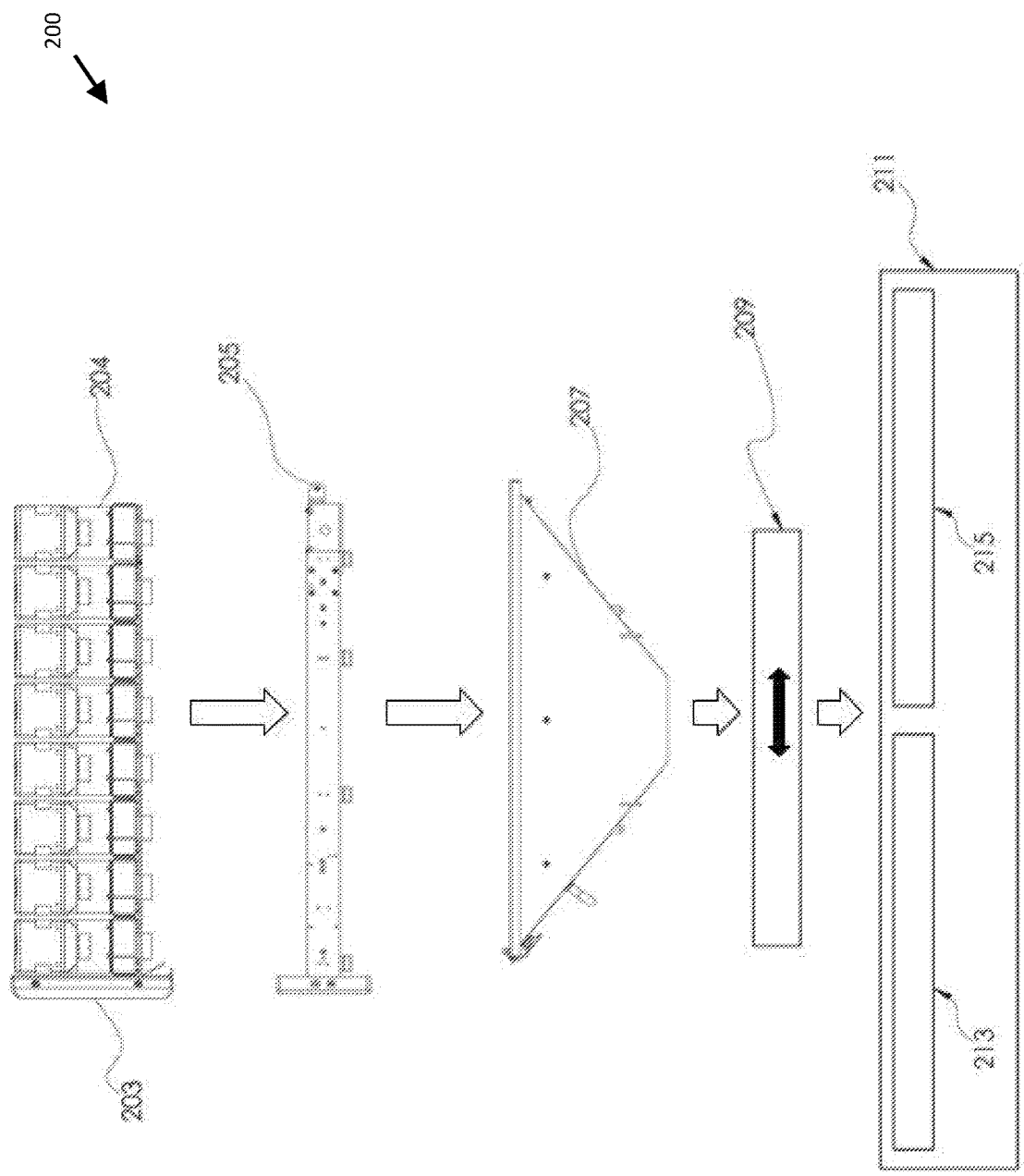
FIG. 2 is a block diagram of some of the components of a robot used for dispensing and packaging a pill, according to some embodiments.

FIG. 2 is a block diagram of some of the components of the machine body of the pill dispensing robot, according to some embodiments. The inner components 200 described in FIG. 2 reside within the outer body of the pill dispensing robot 100 as shown in FIG. 1.

The upper part of the pill dispensing robot 100 includes a canister drawer section 102. This section includes a plurality of canisters drawers 203 and a plurality of canisters 204 within each canister drawer. The upper part of the pill dispensing robot 100 also includes a manual fill tray section 104 and a plurality of manual fill trays 205 within this section.

The dispensing section 106 includes a hopper 207. In one embodiment, the hopper 207 has a wider top and narrower bottom. The inside of the hopper 207 is hollow with a wide opening at the top that allows a pill dispensed from the canister or manual fill tray to enter the hopper and then using gravity drop through its hollow inside and exit the hopper 207 from it narrower opening at the bottom. In yet another embodiment, the hopper 207 may also include a square and hollow tunnel extending from its bottom to prevent pills from bouncing back into the hopper 207 after they are dropped. The hopper 207 may include a camera for counting pills dropped from the hopper 207. Alternatively, the hopper may include a photodiode or some light emitting mechanism that is used to calculate the number of pills dropped through the hopper. The hopper may also include a drop door that can be located at the narrower bottom exit and the drop door may be controlled by a motor to open and close thereby allowing the pills to drop from the hopper at a desired schedule or wait until previously dropped pills have cleared the receptacle below so as to not mix the pills intended for different cells in a blister/pill pack with each other.

The dispensing section 106 also includes a pre-fill tray system 209. This pre-fill tray system 209 may include one or more pre-fill trays that coordinate with each other to receive the pills dropped from the hopper and transfer then from one pre-fill tray to another. Further, a packing plate 211 that includes a plurality of pill packs 213 and 215 are also located in the dispensing section of the robot 100.

The vertical order of arrangement includes canisters 203 and manual fill trays 205 at the top followed by a hopper 207 below it. Alternatively, a small hopper (not shown) can be placed underneath the hopper 207. The arrows pointing downward depict the flow of medications from top to bottom for the Robot 100.

The pre-fill tray system 209 is directly underneath the hopper 207. The pre-fill trays in this section are capable of moving in an X-Y plane as indicated by the arrows shown on 209. Vertically below the pre-fill tray system 209 is the packing plate 211 that can hold a plurality of pill packs 213 and 215.

Figure 3:
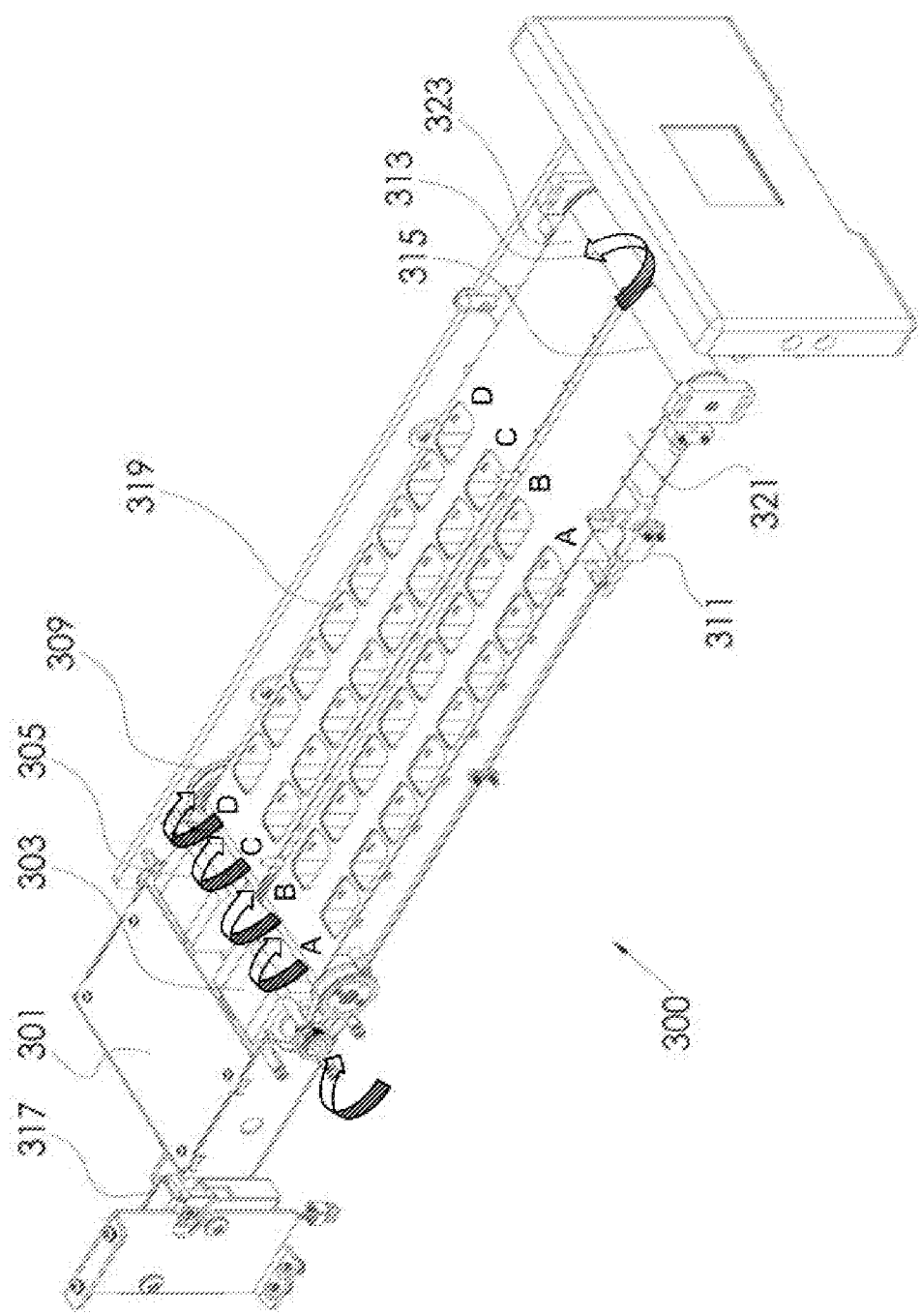
FIG. 3 is a perspective view of a manual fill tray, according to some embodiments.

FIG. 3 is a perspective view of a manual fill tray, according to some embodiments. The manual fill tray 300 includes housing 301, a plurality of motors 303 and 305 coupled to the housing 301, a plurality of pulley-belt mechanisms 309, a plurality of sensors 311, a plurality of pill dispensing belts 313 and 315, and a plurality of openings 319 in each dispensing belt.

The housing is subdivided into a plurality of separate pill storage units. In one embodiment, the housing is divided into two pill storage units 321 and 323, however, other variations are also contemplated. The housing is made from aluminum and the material is treated with solutions that allow safe interactions with medications. Other materials, including plastic, composites, and combinations and treatments are also contemplated.

Each of the two pill storage units includes cavities or slots that allow deposition of pills into the slots. Each of the two pill storage units are independently controlled such that one pill storage unit can operate is a manner independent from the other storage unit. For example, a motor 303 can operate dispensing belt 315 independently from motor 305 operation of dispensing belt 313.

In one embodiment, one of the storage units includes slots arranged in rows and columns. For example, the storage unit may have two rows and eight columns of slots making it a total of sixteen slots for each storage unit. Alternative number of storage units, rows and columns and total number of slots are also contemplated.

The dispensing belt wraps around the storage unit. The dispensing belt includes the same number of openings in the belt as the number of slots in the storage unit. For example, in a 16-slot storage unit, the dispensing belt would also have sixteen openings. In addition to the 16 openings, the dispensing belt includes additional openings for dispensing pills.

The rotation of the dispensing belt is controlled by the operations module of the robot 100. The operations module may direct motor 303 to rotate the dispending belt clockwise or anti-clockwise. The motor may also operate clockwise for a certain period of time until a desired number of pills in the desired slots are dispensed and then switch directions to operate counterclockwise to dispense remaining pills from another set of desired slots in the pill dispensing belt.

The Manual Fill Tray 300 can be in a variety of positions, including a depositing position, a lockdown position, and a dispensing position. The depositing position allows pills to be deposited into the plurality of slots of the storage unit. Pills can either be hand filled into each cavity or deposited using a deposition device, such as a manual tray helper.

When it is in its depositing position, the 16 openings in the dispensing belt are positioned directly above the 16 slots of the storage unit such that the belt section overlaying the slots is open to the above and pills can be deposited through the 16 openings in the dispensing belt into the 16 slots of the storage unit. If the current position of the dispensing belt is not in its dispensing position, the motor may cause the belt to rotate either clockwise or anticlockwise until the 16 openings in the dispensing belt overlay the 16 slots in the storage housing creating an opening to the above.

Further, in its dispensing position, the bottom of the slots is covered by the dispensing belt with no openings on the bottom. In this position, the bottom of the dispensing belt creates a base or floor for each of the slots of the storage unit such that pills deposited in the slot stay within the slot and not fall through. The base of the belt maintains a tight fit with the bottom of the slot such that there is no sagging of the belt below the slot thereby preventing any leakage of pills. The Manual Fill Tray 300 uses tightening mechanisms such as screws and driven pulleys that ensure tight fit between the dispensing belt and the slots thereby providing a floor/base to each slot without any sag.

The belt can also be in a lock-down position. In this position, the opening of the dispensing belt is not above the slots of the storage unit thereby encapsulating each slot from the above so that the slots are closed to the above. This lockdown position is used under multiple conditions. In one instance, the lockdown position is used to prevent any deposition of pills into the slots of the storage unit. The Manual Fill Tray 300 includes verification mechanisms that allow deposition of pills only when allowed by the robot 100 and only after verifying and authorizing the deposition. The verification and authorization methodology is explained below in FIG. 6 below.

The lockdown position may also be employed after pills have been deposited into the slots of the storage units. In this instance, the lockdown position prevents further deposition or taking out of the pills from the slots. Further, the robot 100 may direct the motors to rotate the dispensing belt such that it is in a lockdown position for security reasons, such as unauthorized deposition or take out, or for reasons to prevent any dust or any other materials from entering the slots. In this lockdown position, the bottom of the dispensing belt is positioned such that it creates a base/floor for each of the slots of the storage unit such that pills currently in the slot remain inside the slot and not fall through. As mentioned above, the base of the belt maintains a tight fit with the bottom of the slot such that there is no sagging.

Figure 4:
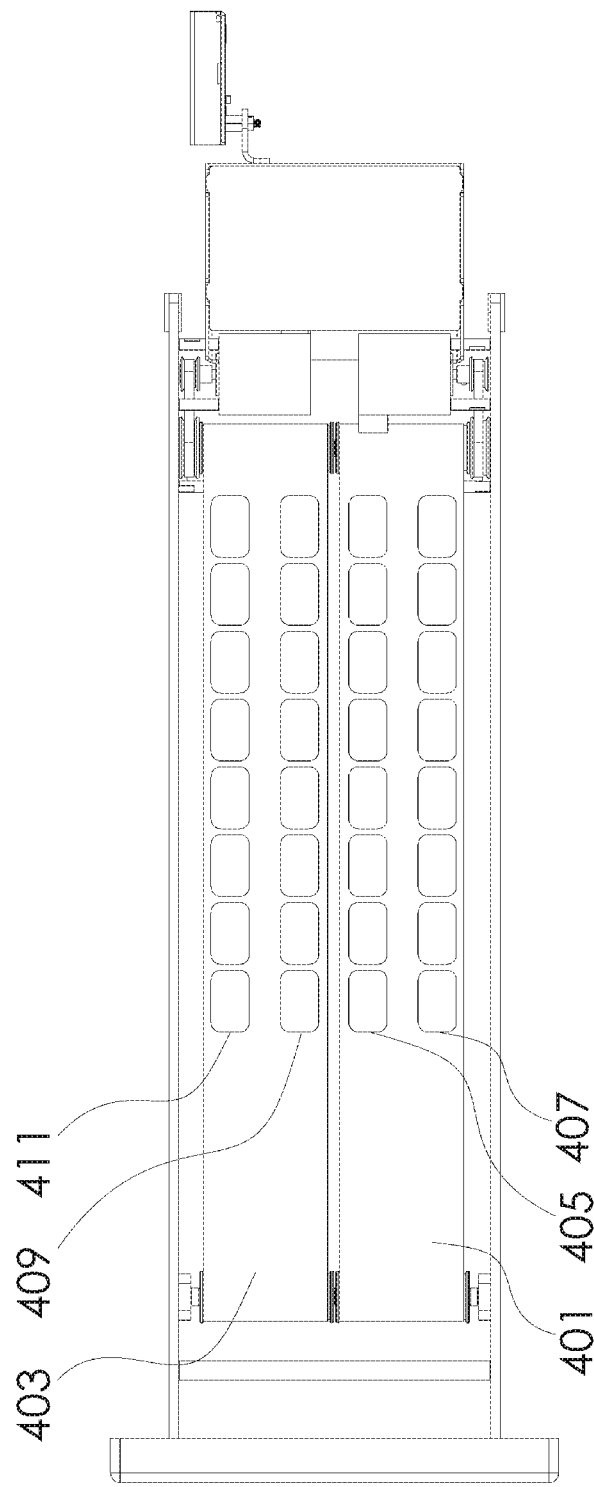
FIG. 4 is a top view of a manual fill tray, according to some embodiments.
Figure 5:
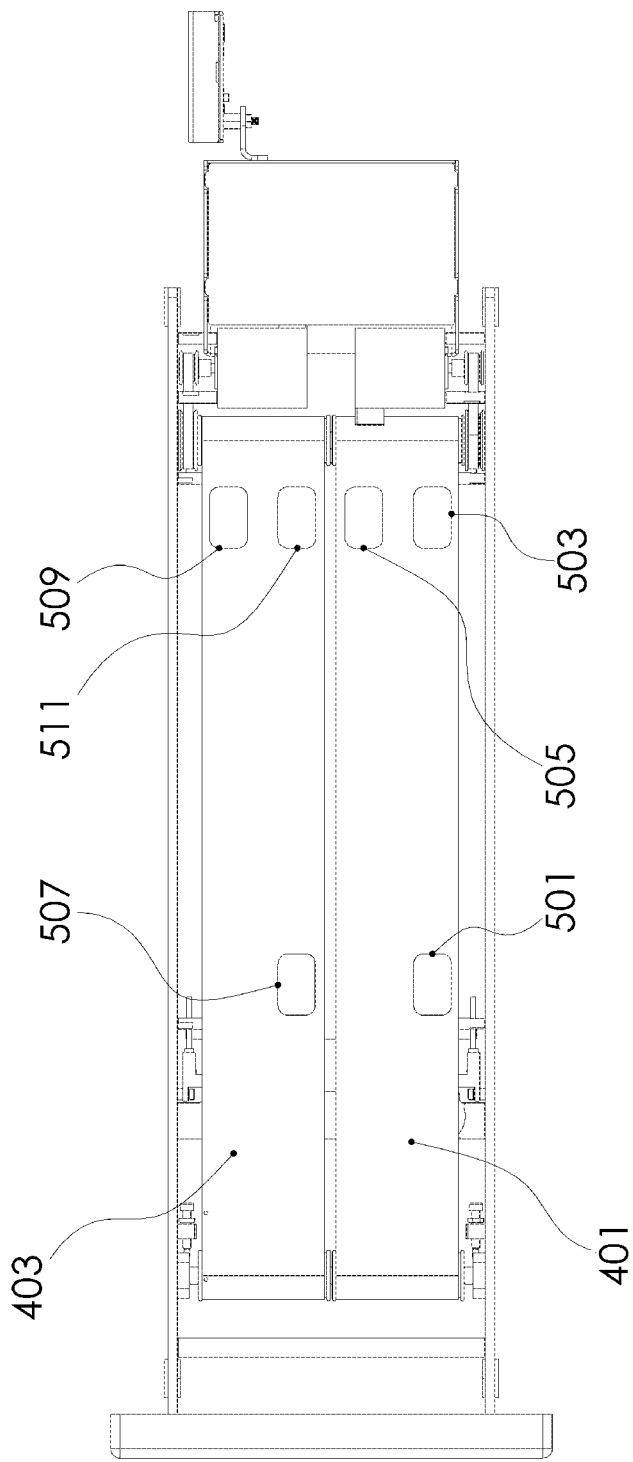
FIG. 5 is a bottom view of a manual fill tray, according to some embodiments.

Yet another position of the manual fill tray 300 is the dispensing position. In this position, the robot 100 directs the motor to rotate the dispensing belt such that a selected opening in the dispensing belt is moved underneath a selected slot of the storage unit thereby allowing only pills from that selected slot to drop therethrough. The openings in the dispensing belt used for dispensing pills are separate from the opening in the dispensing belt that are used for depositing pills. FIGS. 4 and 5 provide additional details on the location of these two types of opening and their displacement in the dispensing belt.

FIG. 4 is a top view of a manual fill tray, according to some embodiments. This figure also depicts the top view of the dispensing belts 401 and 403. Dispensing belt 401 wraps around its own storage unit while dispensing belt 403 wraps around a separate storage unit that is adjacent.

The dispensing belts 401 and 403 include two types of openings. One type of opening is the deposition opening. Openings in rows 405, 407, 409, and 411 are deposition opening. Also, the 16 openings mentioned above in FIG. 3 are an example of the deposition opening.

As mentioned above, these openings in the dispensing belt can be moved through the rotation of the dispensing belt either clockwise or anti clockwise. The displacement of the 16 dispensing openings allows the slots in the storage units to be either open or closed to the above thereby allowing deposition and lockdown positions. Typically, these deposition openings either overlay directly above the slots or can be displaced such that they are further along the storage unit or rotated below the storage unit.

FIG. 5 is a bottom view of a manual fill tray, according to some embodiments. This figure also depicts the bottom view of the dispensing belts 401 and 403. Dispensing belt 401 wraps around its own storage unit while dispensing belt 403 wraps around a separate storage unit that is adjacent.

As mentioned above, the dispensing belt has a deposition opening, which was shown in FIG. 4, and the same dispensing belt has a bottom opening. The bottom opening is the other type of opening in the dispensing belt and is referred to as the dispensing opening. Typically, these openings are at the bottom side of the dispensing belt, however due to belt rotation these may have been displaced to the top side of the belt as well and can be rotated back down to the bottom side of the storage units. In one instance, there are three dispensing openings 501, 503, 505 for dispensing belt 401 and three dispensing openings 507, 509, and 511 for dispensing belt 403. Since both the dispensing belts 401 and 403 can be operated separately and distinct from each other, likewise the dispensing opening can also be displaced independently in each belt.

The three openings in the belt are positioned such that there is one opening 501 that is separate by itself and a pair of openings side by side 503 and 505 placed at a desired horizontal distance from the single opening 503.

The single opening 501 is underneath but is in the same row as the slots in row 407. Likewise, single opening in the dispensing belt of the second storage is also in the same row as the slots in rows 409. The pair of openings in dispensing belt 401 are underneath but in same rows 405 and 407 as the slots above.

Referring back to FIG. 3, the Manual Fill Tray's 300 various positions, i.e. depositing position and lockdown position were explained. Now referring to FIG. 5, yet another position of the manual fill tray 300 is the dispensing position. In this position, the robot 100 directs the motor to rotate the dispensing belt such that a selected opening in the dispensing belt is moved underneath a selected slot of the storage unit thereby allowing only pills from that selected slot to drop therethrough.

For example, opening 501 may be displaced to such that the opening is directly underneath one of the slots in row 407 thereby allowing the pills from that slot to be dispensed. Likewise, pair of openings 503 and 505 may be displaced such that they allow pills from their respective slots, the opening is created underneath them, to be displaced.

Figure 6:
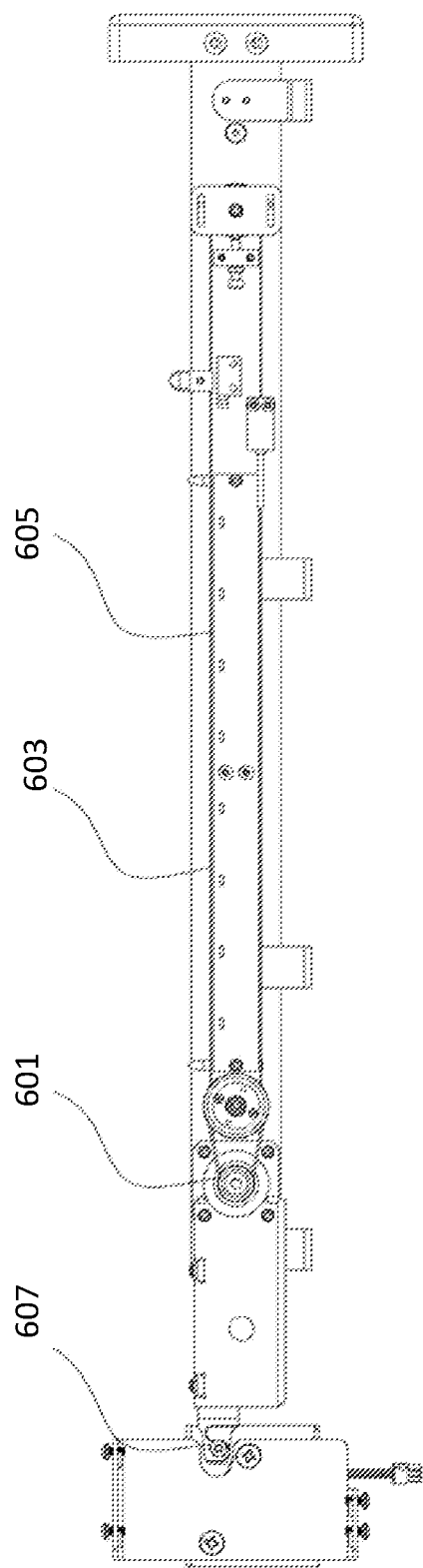
FIG. 6 is a side view of a manual fill tray, according to some embodiments.

FIG. 6 is a side view of a manual fill tray, according to some embodiments. The housing of the manual fill tray 300 includes a plurality of pulleys, tension and alignment mechanisms. Pulley-roller 601 is rotated by the motor in each storage unit to displace the dispensing belt in either a clockwise or an anticlockwise direction. Tension and alignment mechanisms 603 and 605 are placed in various sections of the housing at desirable distances from each other such that they provide a securing mechanism for the dispensing belt as well as provide tension by stretching and movably securing the belt so that there is a snug and tight fit between the dispensing belt and the bottom of the slots thereby preventing any slag in the dispensing belt or any gap in-between.

The manual fill tray 300 also includes a Radio Frequency Identification Reader (RFID Reader) according to some embodiments. The RFID reader is capable of reading radio frequency identification (RFID) tag of a device, such as a helper tray, that is used for depositing pills into the slots of the storage units.

The RFID tags on the helper tray, or such device used for depositing pills into the manual fill tray, contains electronically stored information that is transmitted to them from the robot 100. The RFID tag relates to a different drug or medicine or prescription plan associate with a patient. The robot 100 uses RFID reader on manual fill tray to read the RFID tag on the depositing device and determines if there is a match. Since the information from the RFID tag indicates the type and quantity of pills located in the depositing device, a match essentially confirms that these are the prescribed pills that are intended for a patient for whom the dispensing is being performed and therefore allows deposition.

Once a match is confirmed, i.e. a determination has been made that the pills matches the prescription that was prescribed for the patient and according to the plan, the dispensing belt is displaced such that the 16-deposition opening are displaced directly above the slots thereby creating an opening to the above and allowing an authorized deposition of the pills. This locking-unlocking mechanism, i.e. opening of slot to the above or closing them, along with RFID verification prevents errors as well as tampering with or theft of medications.

FIG. 7A depicts a top view and FIG. 7B depicts a bottom view of the pill dispensing belt in its initial position, according to some embodiments. The initial position, also referred to above as the deposition or depositing position is used for depositing of pills into the slots of the storage units.

FIG. 7A depicts the top view of the pill dispensing belt in its initial starting position. It the starting position, the belt overlays the slots such that each slot is open to the above thereby allowing deposition of pills into the open slots. As mentioned above, this can be accomplished by the 16 openings on the dispensing belt 700 to directly overlay the 16 slots. These 16 openings in the dispensing belt 700 are also referred to as the depositing or deposition openings.

The deposition in this initial position may be manual or through another apparatus that may fit above and be aligned with the open slots of the manual fill tray. As it can be seen in FIG. 7A, in this starting or deposition position, the slots 701-713 are shown open to the above.

FIG. 7B depicts the bottom view of the pill dispensing belt in its initial position, as referred to earlier as the depositing position. There are three dispensing openings 717, 719, and 721 in the dispensing belt 700. In this position, the dispensing openings 717, 719, and 721, which are at the bottom of the dispensing belt 700 are positioned such that they are not underneath any slots 701-715.

FIG. 7C depicts a side view of the pill dispensing belt in its initial position, according to some embodiments. The side view shows a cross section of the dispensing belt 700 through the first row of slots, i.e. slots 703, 707, 711 to 715.

This cross section depicts slot 703 is aligned with deposition opening 727, slot 707 is aligned with deposition opening 729, slot 711 is aligned with deposition opening 731, slot 715 is aligned with deposition opening 733 thereby making all the slots in both the rows of the storage unit open to the above by having the openings in top portion 723 or the dispensing belt 700 overlay directly on top.

While the top of the slots is open to the above, the bottom of the slots is in a closed position. The bottom section 725 of the dispensing belt in this position, as shown in the cross section through first row as mentioned above, depicts the two dispensing slots 717 and 719 away from the slots. The figure also shows that the bottom of the dispensing belt 725 in this state is tightly hugging the slots forming a base or a floor such that the pills in each slot are retained therein.

FIG. 7D is a detailed view of the pill dispensing belt in its initial position, according to some embodiments. In this depositing position, the top of the slot is open for depositing while the bottom of the slot is closed forming a base. Once deposited, the pills stay in this slot.

FIG. 8A depicts a top view and FIG. 8B depicts a bottom view of the pill dispensing belt in its dispensing position, according to some embodiments. As indicated above, there are two independently operable storage units and dispensing belts in each Manual Fill Tray 300. This Figure depicts a cross section through just one of the two storage units and the dispensing belt to illustrate the operation and positioning of the openings in the dispensing belt in the dispensing position. The second storage unit and dispensing belt also operates in the same manner; however, it may operate on a different schedule than the belt depicted in FIG. 8A-D.

In its dispensing position, the robot 100 directs the motor to displace the dispensing belt 700 by rotating it clockwise until the dispensing opening 717 is displaced directly underneath slot 703.

FIG. 8A depicts the top view of the pill dispensing belt in its dispensing position, according to some embodiments. In this position, the dispensing belt 700 has advanced by being displaced clockwise. By this advancement, all the opening in the displacement belt, both the deposition openings as well as the dispensing openings 717, 719, and 721 have also been displaced. The dispensing opening 717, which was earlier in its initial position in a spot that is not underneath any slot has not been displaced to be underneath slot 703. Likewise, dispensing openings 719 and 721 that were underneath the storage unit have been displaced such that they were rotated clockwise until they are not placed above the storage unit but not above any slot.

FIG. 8B depicts a bottom view of the pill dispensing belt in its dispensing position, according to some embodiments. In its dispensing position, the dispensing opening 717 has been displaced towards the left due to the rotation of the dispensing belt 700.

In order for the Manual Fill Tray 300 to be in the dispensing mode, the dispensing opening 717 needs to be underneath a slot containing pills such that it provides an opening to the bottom of the slot. One of the methods of accomplishing this would be to rotate the dispensing belt 700 until the dispensing opening is directly underneath the slot 703 thereby removing the base underneath the slot 703 and creating an opening through which pills contained in the slot 703 fall through by force of gravity into the next receptacle, which can be a hopper.

Also, as it can be seen in the bottom view of FIG. 8, there is no other dispensing opening, or any other opening, in the dispensing belt at this instance. This prevents any other pills from any other slots from being dropped therethrough. So the dispensing belt continues to act as a base/floor for all the slots except the slot which is intended to be dispensed. Only the intended slot is opened to the bottom and then pills are dropped. The intended slot, from the plurality of slots, is selected by the Robot 100 based on a schedule of dispensing. The schedule of dispensing relates to which cell or a pill pack is being filled by the robot, i.e. if the robot is currently filling a particular cell in the pill/blister pack that is to be taken by the designated patient and that particular cell is intended to contain pills to be taken on Thursday morning, then the slot opened during dispensing would contain the exact pills needed to fill that particular cell in the pill/blister pack for Thursday morning. Likewise, the dispensing opening 717 can be displaced to other slots, such as slots 707, 711 to 715, i.e. all the slots in that row one slot after another.

FIG. 8C depicts a side view of the pill dispensing belt in its dispensing position, according to some embodiments. This side view is a cross section through the first row of a storage unit of the Manual Fill Tray 300. This cross section is through the slots that are in the first row as well as any openings in the dispensing belt that are also in the first row of this storage unit.

The dispensing belt 700 is shown for the Manual Fill Tray 300 in its dispensing mode. In this instance, the dispensing belt 700 has been displaced by being rotated clockwise. The displacement has been stopped when displacement opening 717 is directly underneath slot 703 thereby allowing the pills held therein to drop below. At the same time, the dispensing opening 719, which was below the storage unit and towards it left end has been displaced through rotation of the dispensing belt 700 such that it is not on the top of the storage unit. At this instance the dispensing opening 719, although on top of the storage unit, is not directly above any slot. The purpose of dispensing opening 719 is so that the belt may be rotated counter-clockwise until dispensing opening 719 is directly underneath slot 715 to allow pills from it to fall therethrough.

Likewise, dispensing opening 721 is also used for dispensing pills from the slots, however, from the slots that are located in the second row of the storage unit. In operation, in order to dispense pills located in slots 713, 709, 705, and 701, the robot would cause the motor in this storage unit to rotate the dispensing belt 700 counter clockwise until the dispensing opening is underneath slot 715, and then again until it is under slot 709, and then 705 and then 701 thereby emptying pills from each slot one slot at a time and in accordance with the dispensing schedule as mentioned above.

FIG. 8D is a detailed view of the pill dispensing belt in its dispensing position, according to some embodiments. The detailed view depicts the dispensing opening 717 being placed directly underneath the slot 703 and causing the pills inside the slot to drop through. The detailed view also shows mechanisms 801 that are used in various locations of the storage unit for securing the dispensing belt 700 such that the belt stays in place as well as provides for a tight fit with the base of the plurality of slots to avoid any leakage or lag.

FIGS. 9A-9C are bottom views the pill dispensing belt during its various stages dispensing using a single opening, according to some embodiments. The Manual Fill Tray 300, as mentioned above, contains a plurality of storage units. Each storage unit includes a housing having a plurality of slots and a dispensing belt having a plurality of deposition openings and dispensing openings.

In one embodiment, FIG. 9A depicts the Manual Fill Tray 300 in its initial position. Here, the Manual Fill Tray 300 includes a first storage unit 901. The storage unit 901 includes a dispensing belt 902. The first storage unit also includes a plurality of slots (not shown in FIG. 9 but discussed and shown in earlier Figures) for housing medical pills. The dispensing belt 902 includes a plurality of deposition openings (not shown in FIG. 9 but discussed and shown in earlier Figures) and a plurality of dispensing openings 905, 907, and 909.

The Manual Fill Tray 300 also includes a second storage unit 903 that includes a dispensing belt 904. The second storage unit also includes a plurality of slots (not shown in FIG. 9 but discussed and shown in earlier Figures) for housing medical pills. The dispensing belt 904 includes a plurality of deposition openings (not shown in FIG. 9 but discussed and shown in earlier Figures) and a plurality of dispensing openings 911, 913, and 915.

The first and second storage units and their respective dispensing belts are operated independent from each other. For example, the robot may decide to dispense pills from the first or the second storage unit by either starting with the first storage unit or starting with the second storage unit. The robot may also decide to operate them at the same time. The robot may also decide to rotate the dispensing belt for the first storage unit clockwise while rotating the dispensing belt for the second storage unit counterclockwise. The robot may schedule the dispensing of the storage units based on a dispensing schedule to match the filling of a blister pack intended for a specific patient. Likewise, dispensing opening in the first dispensing belt may be displaced separate and independent from dispensing opening in the second dispensing belt.

FIGS. 9A-9C are one embodiment of using a single dispensing opening. In its initial stage, FIG. 9A shows the position of the single openings 905 and 911 in dispensing belts 902 and 904 respectively. The initial position may be a lockdown state for the manual fill tray 300 or any other state that is not a dispensing state. Although the figure shows the single openings to the far right during the initial stage, the single openings of the dispensing belts may also be located anywhere else but not directly underneath any slot during the initial stage. Further, during the initial stage, the pair of dispensing openings may be located to the far left of the dispensing belt. Other locations are also contemplated, however, the pair of openings in the initial stage may not be directly underneath a slot.

FIG. 9B depicts movement of the single occurs when the dispensing belt is in motion. In one embodiment, the dispensing belt 902 is rotated clockwise. The rotation causes the dispensing opening 905 to move left and come directly underneath a slot holding the pills. Likewise, dispensing opening 911 in dispensing belt 904 may also be displaced clockwise to come directly underneath a slot holding the pills. The displacement of displacement openings 905 and 911 may be according to a schedule of dispensing and not depended upon each other.

For example, as show, dispensing opening 905 may be dispensing pills from a second slot in its row while dispensing opening 911 may be dispensing pills from the first slot in its row. Since each dispensing is associated with a cell in a blister/pill pack, only pills intended for that cell may be dispensed at a time. This would prevent any mixing of medications from multiple slots. As such, while dispensing belt 902 is dispensing through it dispensing opening 905 for the second slot, dispensing belt 904 may be on hold and not dispensing any pills until the dispensing of that cell in a blister/pill pack is completed. However, if the pill intended for a particular cell in a blister/pill pack are housed in both storage unit 901 and 903 a slot in storage unit 901 and a slot in storage unit 903 may be dispensed together.

The robot employs various holding mechanisms through its hopper and pre-fill trays that allow dispensing of multiple cells in a blister/pill pack at a time. As such, once the pills for a particular cell in a blister/pill pack are dispensed, the manual fill tray 300 does not need to wait for the pills to make their way all through the system and into their cell in a blister/pill pack, they can start dispensing based on the dispensing schedule and dispense the pills intended for the next cell in a blister/pill pack thereby avoiding any delays and leading to a faster and efficient system.

FIG. 9C depicts movement of the single opening as it dispenses pills from the last slot in its row. As mentioned above, the single opening 905, 911, are displaced one slot at a time until all the slots in its row are dispensed. The initial placement/deposition of the pills in the slots follow a dispensing logic that allows the sequential in-line dispensing from one slot to the next in a single row. The robot and its systems pre-calculate and identify pills for each slot in the manual fill tray 300 in its planning stages so that dispensing can be perform in the sequential in-line slot by slot method.

Figure 10A:
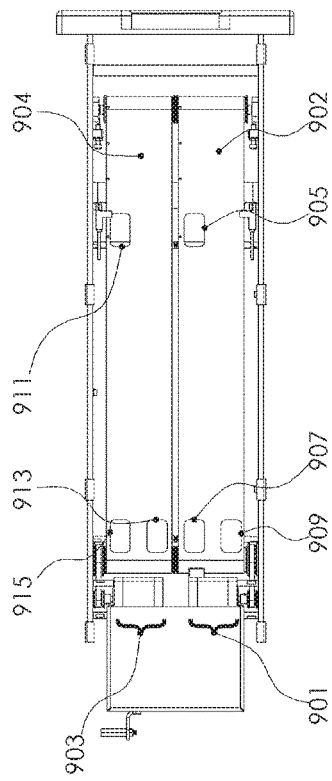
FIGS. 10A-10C are bottom views the pill dispensing belt during its various stages dispensing using pair of openings, according to some embodiments.
Figure 10B:
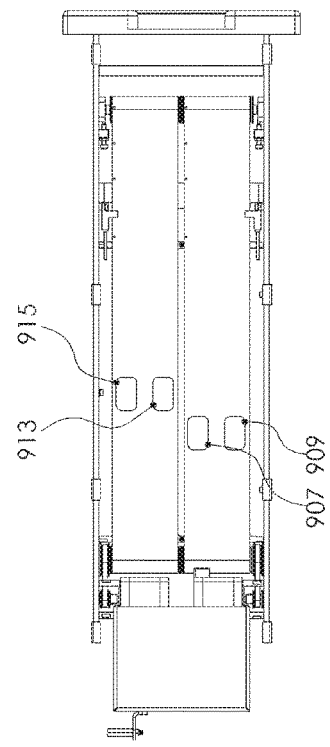
Figure 10C:
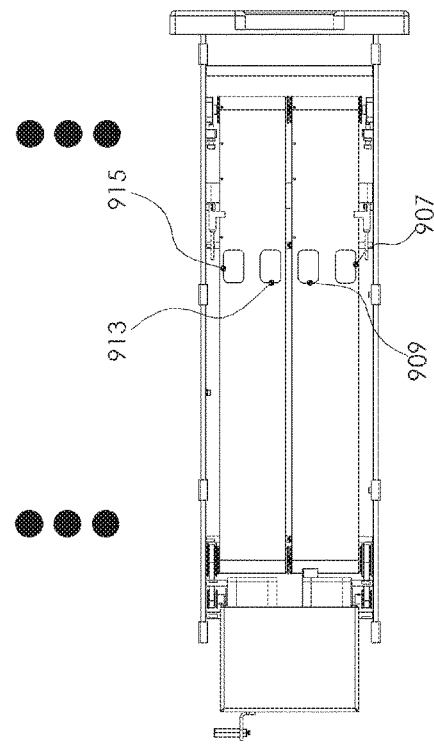

FIGS. 10A-10C are bottom views the pill dispensing belt during its various stages dispensing using pair of openings, according to some embodiments. FIGS. 10A-10C are similar in operation to 9A-9C except that they utilize the pair of dispensing openings instead of the single openings mentioned above.

FIG. 10A shows the position of the pair or openings 913-915 and 907-909 as well as the single openings 911 and 905 in dispensing belts 904 and 902 respectively. As mentioned above, the initial position may be a lockdown state for the manual fill tray 300 or any other state that is not a dispensing state. Although the figure shows the openings in a particular configuration during the initial stage, the openings may also be located anywhere else but not directly underneath any slot during the initial stage.

FIG. 10B depicts movement of the openings in the dispensing belt. In one embodiment, first the single opening 905 and 907 are utilized to empty pills in the slots, one slot at a time, in a slot by slot in line sequential order, until all the slots that are located in the same row as the single opening 905 and 907 are emptied. Once the first row is emptied, then the pills in the second row still remain. At this point, the dispensing belts may be rotated counter-clockwise until the pair of dispensing openings come directly underneath the first pair of slots from the left. FIG. 9B shows the pair of slots 907 and 909 being placed directly under the far-left par of slots.

Since dispensing opening 907 is essentially in the same row as single dispensing opening 905, when the pair of dispensing openings 907 and 909 reach their first slots, the slots in the row of 907 should have already been emptied earlier through the displacement of single opening 905 as discussed in FIGS. 9A-C. As such, the displacement of the dispensing opening pair 909, 907 would result in emptying all the slots in the second row, one slot at a time, in a slot by slot in line sequential order, until all the slots the second row are emptied. Alternatively, other methodologies that still have pills left in certain slots to the far-left in the first row may also be emptied, if not done so already by the single opening, by displacing the multiple pair of openings.

FIG. 10C depicts movement of the pair of opening as it dispenses pills from the far-left all the way to the far-right. As mentioned above, the pair of opening 907-909 and 913-915, 911, are displaced one slot at a time until all the slots in its row are dispensed.

Figure 11:
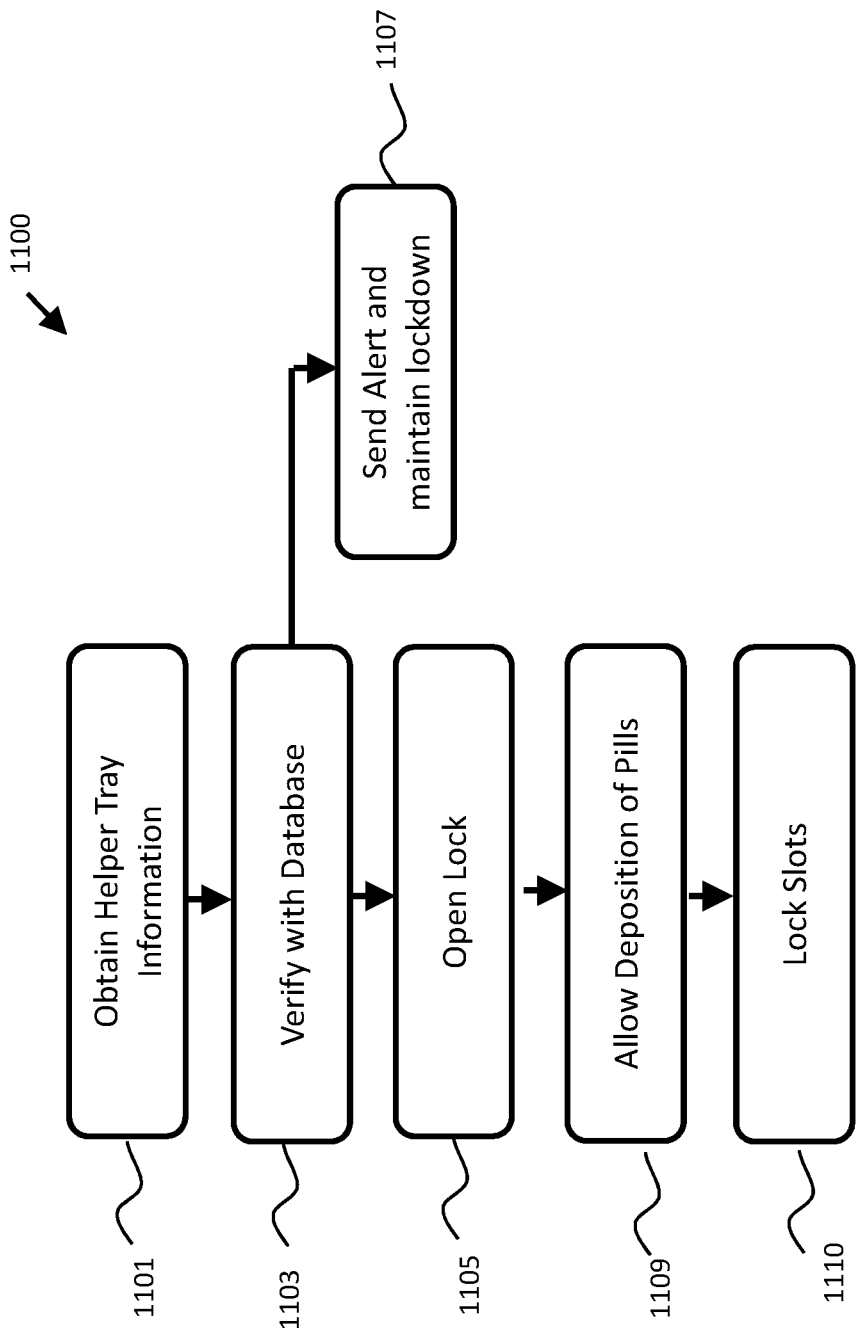
FIG. 11 depicts a flowchart for verification and authentication of pills being deposited into the Manual Fill Tray, according to some embodiments

FIG. 11 depicts a flowchart for verification and authentication of pills being deposited into the Manual Fill Tray, according to some embodiments. The robot allows pills to be deposited into the Manual Fill Tray through use of devices that populate several slots in the manual fill tray at a time thereby making it a fast and efficient process. This procedure allows the manual fill tray to be filled without an attendant having to stand by the robot and manually fill each slot by hand, one slot at a time, and having to stop the dispensing of the robot during the fill. The procedure used allows for a volume fill or one or many manual fill trays in a fast-paced manner with minimal or no stoppage to the dispensing thereby making it an efficient system.

At 1101, a device, such as a Helper Tray, is used for filling a Manual Fill Tray 300. The helper tray may have the same number of slots as that in a manual fill tray and positioned in the same configuration as the manual fill tray such that all the slots in the Manual Fill Tray 300 can be filled instantaneously by the helper tray.

The Manual Fill Tray 300 includes an radio frequency identification reader, an RFID reader. The Manual Fill Tray 300 also includes mechanisms, protrusions, and indentation that allow the helper tray to be placed, fitted, and locked above the Manual Fill Tray 300. At 1101, the RFID reader of Manual Fill Tray 300 reads an RFID tag located on the helper tray and obtains relevant information. The information includes patient data, drug data, patient's prescription plan and other data relevant and required for dispensing.

At 1103, the information obtained is transmitted to the robot 100 where it is analyzed to ensure a match. Since the information from the RFID tag indicates the type and quantity of pills located in the depositing device, a match essentially confirms that these are the prescribed pills that are intended for a patient for whom the dispensing is being performed and therefore allows deposition.

At 1105, once a match is confirmed, i.e. a determination has been made that the pills matches the prescription that was prescribed for the patient and according to the plan, the dispensing belt is displaced such that the 16-deposition opening are displaced directly above the slots thereby unlocking the slots by creating an opening to the above.

However, at 1107, if a match is not confirmed, then the robot may provide an alert that is either audible or visual. The robot may also utilize certain displays coupled with the Manual Fill tray to provide guidance to the operator such that the operator may go any get the correct helper tray that is associated with the pills being dispensed.

At 1109, pills from the slots of helper tray are allowed to be dispensed into the associated slots of the Manual Fill tray.

At 1110, once the filling of the Manual Fill Tray is completed, the robot may cause the dispensing belt to rotate again such that the slots are locked and no longer open for dispensing or accessible.

Figure 12:
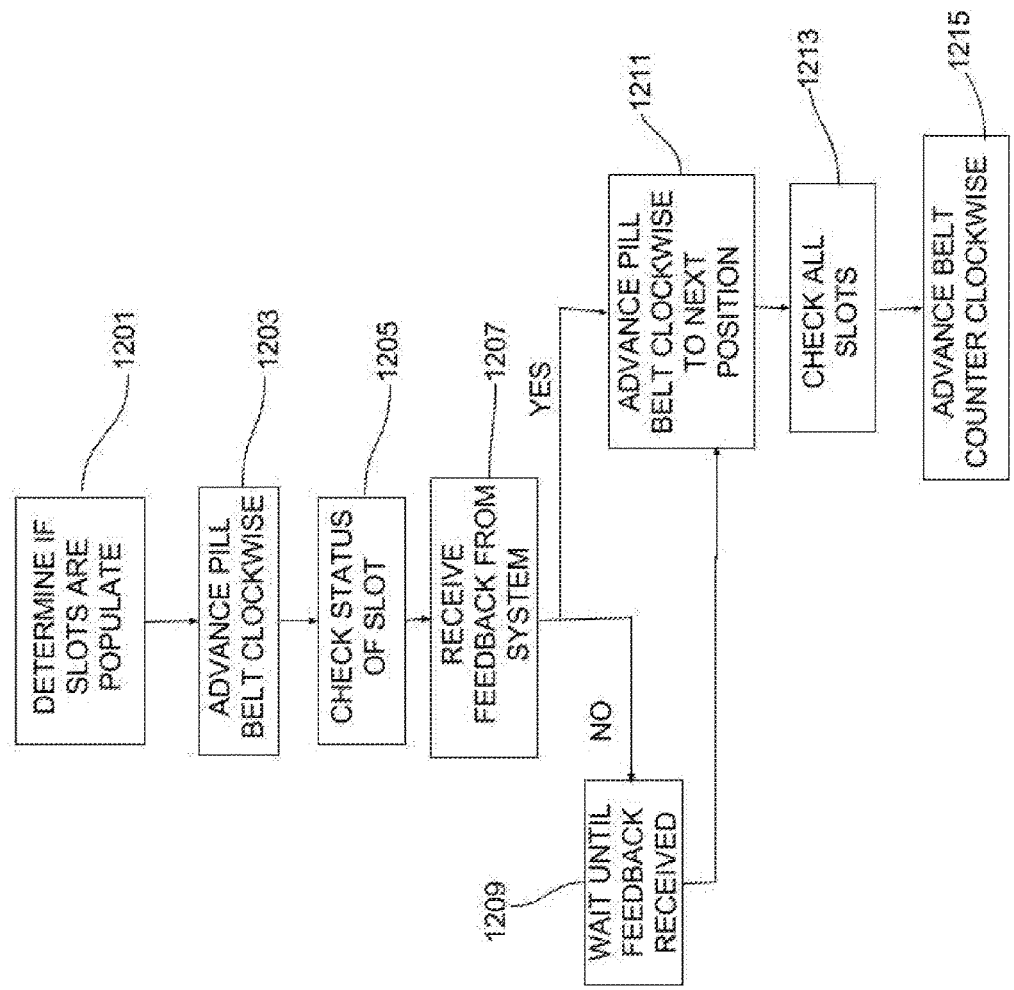
FIG. 12 depicts a flowchart for dispensing medications using a pill dispensing belt, according to some embodiments.

FIG. 12 depicts a flowchart for dispensing medications using a pill dispensing belt, according to some embodiments. References to the pill dispensing belt, slots, dispensing openings, storage units, and other components are mentioned in figures above.

At 1201, the robot determines if the slots in storage units 901 and 903 are populated with the required pills. The robot performs this check on all the manual fill trays that are housed inside the robot.

At 1203, the robot causes the motor to rotate a dispensing belt clockwise. The rotation causes a single opening in the dispensing belt, also referred to as the single dispensing opening, to be displaced such that is comes directly underneath a first slot housing pills. The slot is in the same row as the single dispensing opening. The displacement causes the pills in the first slot to drop from below and into a hopper (or another receptacle).

At 1205, the robot checks the status of the first slot. This checking ensures that all the pills in the slot have been dispensed. Various mechanisms, such as through sensors, visual or camera checks can be employed to confirm that the slot has been emptied.

As mentioned above, at 1207, a feedback is received confirming that the pills have been dispensed. As mentioned above, the hopper also includes camera or alternatively other pill counting mechanisms. Since the robot has knowledge of exact number and type of pills in each slot, the hopper counting mechanisms may also provide a feedback to ensure that the particular slot has been emptied when all the pills in the slot have been confirmed by the hopper as dispensed using its counting mechanisms.

At 1209, if the feedback, or through other means, the robot determines that the pills have not been dispensed, or that only a partial number of pills have been dispensed, then the robot checks the alignment of the opening in the dispensing belt with the slot holding the pills. The robot may make a few attempts to re-align or to displace the dispensing belt back and forth until a confirmation is received that all the pills from that slot have been dispensed. The robot may wait until feedback is received and confirmed that pills have been dispensed.

At 1211, once its confirmed that the pills from the first slot have been dispensed, then the robot causes the dispensing belt to continue its rotation clockwise to the next slot.

At 1213, the process may continue until all the slots in the row of the single opening have been dispensed. The robot would check each clot at a time, obtain feedback and confirmation before advancing to the next slot. It may also do this process one slot at a time in a sequential order matching the dispensing schedule.

At 1215, once all the slots in the row of the single opening have been dispensed, the robot causes the dispensing belt to rotate counter-clockwise. The rotation would cause a pair of openings in the dispensing belt to come directly underneath slots of first and second row. Since the slots in the first row would have already been dispensed, this process would allow disposing of all the slots in the second row, one slot at a time.

Figure 13:
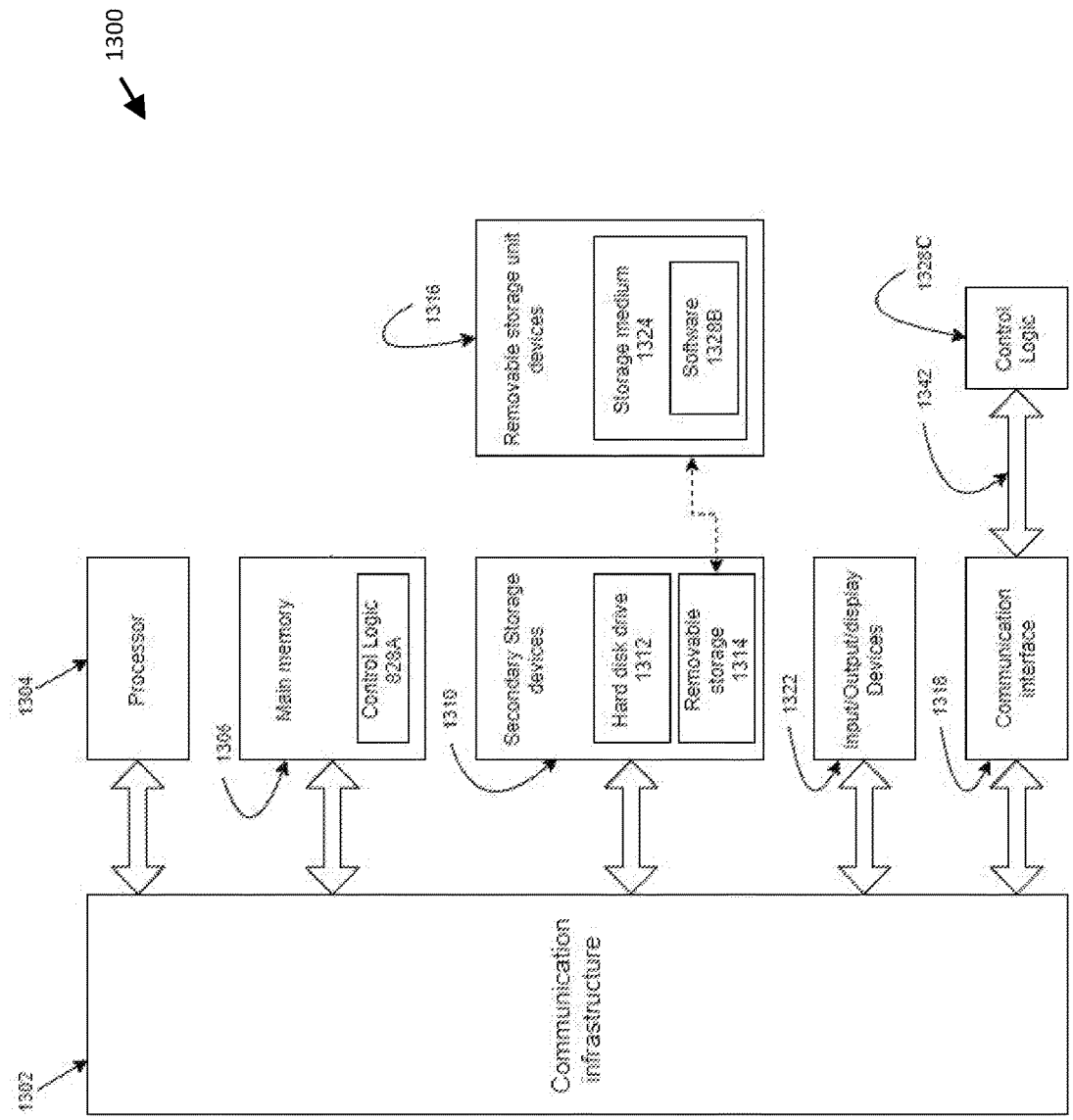
FIG. 13 is a block diagram of a node that can implement the control module of the pill dispensing robot, according to some embodiments.

FIG. 13 is a block diagram of a computer system that can is used in operation of the pill dispensing robot, according to some embodiments. The embodiments described herein, including systems, methods/processes, and/or apparatuses, may be implemented using well known servers/computers, such as computer 1300 shown in FIG. 13. For instance, elements of example pill dispensing robot 100, including any of computing devices or any elements thereof, each of the steps and the functionality described in this document can each be implemented using one or more computers 1300.

Computer 1300 can be any commercially available and well-known computer capable of performing the functions described herein, such as computers available from International Business Machines, Apple, Sun, HP, Dell, Cray, etc. Computer 1300 may be any type of computer, including a desktop computer, a server, tablet PC, or mobile communication device, etc.

As shown in FIG. 13, computer 1300 includes one or more processors (e.g., central processing units (CPUs)), such as processor 1304. Processor 1304 may include any modules and/or layers of described in the Figures herein, and/or any portion or combination thereof, for example, though the scope of the embodiments is not limited in this respect. Processor 1304 is connected to a communication infrastructure 1302, such as a communication bus. In some embodiments, processor 1304 can simultaneously operate multiple computing threads.

Computer 1300 also includes a primary or main memory 1306, such as a random access memory (RAM). Main memory has stored therein control logic 828A (computer software), and data.

Computer 1300 also includes one or more secondary storage devices 1310. Secondary storage devices 1310 include, for example, a hard disk drive 1312 and/or a removable storage device or drive 1314, as well as other types of storage devices, such as memory cards and memory sticks. For instance, computer 1300 may include an industry standard interface, such as a universal serial bus (USB) interface for interfacing with devices such as a memory stick. Removable storage drive 1314 represents a floppy disk drive, a magnetic tape drive, a compact disk drive, an optical storage device, tape backup, etc.

Removable storage drive 1314 interacts with a removable storage unit 1316. Removable storage unit 1316 includes a computer useable or readable storage medium 1324 having stored therein computer software 1328B (control logic) and/or data. Removable storage unit 1316 represents a floppy disk, magnetic tape, compact disc (CD), digital versatile disc (DVD), Blue-ray disc, optical storage disk, memory stick, memory card, or any other computer data storage device. Removable storage drive 1314 reads from and/or writes to removable storage unit 1316 in a well-known manner.

Computer 1300 also includes input/output/display devices 1322, such as monitors, keyboards, pointing devices, etc. Computer 1300 further includes a communication or network interface 1320. Communication interface 1318 enables computer 1300 to communicate with mobile devices. For example, communication interface 1318 allows computer 1300 to communicate over communication networks or mediums 1322 (representing a form of a computer useable or readable medium), such as local area networks (LANs), wide area networks (WANs), the Internet, etc. Network interface 1320 may interface with remote sites or networks by using wired or wireless connections. Examples of communication interface 1318 include but are not limited to a modem, a network interface card (e.g., an Ethernet card), a communication port, a Personal Computer Memory Card International Association (PCMCIA) card, etc.

Control logic 1328C may be transmitted to and from computer 1300 by using the communication medium 1342. Any apparatus or manufacture comprising a computer useable or readable medium having control logic (software) stored therein is referred to herein as a computer program product or program storage device. This includes, but is not limited to, computer 1300, main memory 1306, secondary storage devices 1310, and removable storage unit 1316. Such computer program products, having control logic stored therein that, when executed by one or more data processing devices, because such data processing devices to operate as described herein, represent embodiments of the invention. For example, Control logic 1328C may be used to align the top pre-fill tray with the bottom pre-fill tray and in the process, take readings, provide feedback, and direct the hardware component to move in the desired direction to ensure alignment. Additionally, the control logic 1328C may be used in any of the flowcharts or operations that require a decision-making step before dispensing the pills to the next stage.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims. The detailed description also mentions that the robot causes certain operations to occur, these may be through its operations module, the computer in FIG. 13, and decision-making logic therein. The detailed description also refers to two storage units within each manual fill tray, and a certain number of slots, a certain number of dispensing belts, and a certain number of openings in the dispensing belts, however, the invention is not so limited and other configurations and numbers are also contemplated.

What is claimed is:

1. A pill dispensing system comprising:
   a plurality of canisters configured to store and dispense one or more pills, wherein, the plurality of canisters are housed inside a first slidable drawer,
   a plurality of manual fill trays configured to store and dispense one or more pills, wherein the manual fill tray is housed inside a second slidable drawer, wherein each manual fill tray includes a plurality of pill dispensing sections, wherein each pill dispensing section includes a plurality of pill slots, including, a first pill slot and a second pill slot, wherein the plurality of pill slots are adjacent to each other and each pill slot is separated from its neighboring pill slot by a wall, wherein each slot is a hollow cavity that is selectively open to the above and selectively open at its bottom and allows for deposition of pills through its top and dispensing of pills from its bottom, wherein the manual fill tray includes a Radio Frequency (RFID) reader;
   a flexible belt coupled to each pill dispensing section, wherein the flexible belt includes a plurality of dispensing openings, wherein the flexible belt wraps around its pill dispensing section, wherein the flexible belt provides a base for the desired pill slots such that the pills held in the desired pill slot do not fall through from its bottom opening;
   a motor operatively connected to each pill dispensing section, wherein the motor is capable of displacing the flexible belt such that a desired dispensing opening in the flexible belt is displaced to align underneath a desired pill slot thereby removing the base from the desired pill slot and creating an opening at its bottom to allow the pills from the desired slot to fall through and be dispensed;
   a communication module that operates the motor and displaces the flexible belt, wherein the communication module communicates with other systems in the pill dispensing system to determine the pill deposition and pill dispensing schedule and operates the motor and flexible belt in accordance with the pill deposition and pill dispensing schedule;
   a hopper system, wherein the hopper system is configured to receive one or more pills dispensed from the manual fill tray and/or the canister and further dispense the received pill from its bottom;
   a pre-fill module, wherein the pre-fill module is configured to receive one or more pills dispensed from the hopper system and further dispense the received pill from its bottom; and
   a packing plate having a plurality of pill packs for receiving the pills dispensed from pre-fill module, wherein, the pill packs includes a plurality of slots for receiving pills, wherein the communication module controls the navigation of the pill through the pill dispensing system such that the pill makes their way from the manual fill tray and/or the canister, through the hopper system and the pre-fill module, and into a desired slot in the pill pack.

2. The pill dispensing system of claim 1, wherein the communication module communicates with the hopper system to determine whether the pills dispensed from the first pill slot of the manual fill tray into the hopper system have cleared the hopper system by being further dispensed from the hopper system to a receptacle beneath the hopper system, and upon determination that the pills have been cleared the hopper system, causing the motor to operate and the flexible belt to be displaced such that the desired dispensing opening from the flexible belt is displaced underneath the second slot of the manual fill tray thereby causing the pills from the second slot to be dispensed into the hopper system.

3. The pill dispensing system of claim 1, wherein the RFID reader is used for reading an RFID tag of a helper tray, wherein the helper tray stores pills that are associated with a prescription for a specific patient, wherein the RFID reader of the manual fill tray reads the RFID tag of the helper tray to determine if the pills housed in the helper tray match the prescription that is being dispensed by the pill dispensing system.

4. The pill dispensing system of claim 3, wherein upon confirmation of a match, the dispensing belt of the manual fill tray is displaced such that the pill slots of the manual fill tray are opened thereby allowing a transfer of pills from the helper tray to the manual fill tray.

5. The pill dispensing system of claim 3, wherein the RFID tag includes prescription, medication, or medical pill information that is associated with a specific patient.

6. The pill dispensing system of claim 1, wherein the plurality of pill slots of the manual fill tray mirrors a plurality of pill slots of a pill pack that is designated to be filled by the pill dispensing system.

7. The pill dispensing system of claim 1, wherein the communication module communicates with various components of the pill dispensing system, the motor, and the RFID reader to selectively operate the manual fill tray in a desired mode.

8. The pill dispensing system of claim 7, wherein the desired mode is selected from a lockdown mode, a storage mode, or a dispensing mode.

9. The pill dispensing system of claim 8, wherein the desired mode is lockdown mode, wherein in its lockdown mode, the plurality of pill slots of the pill module are closed to the above and below by the flexible belt acting as a cover as well as a bottom each of the plurality of pill slots thereby preventing any pills from entering the plurality of pill slots from the above or dispensing from the bottom of plurality of pill slots.

10. The pill dispensing system of claim 8, wherein the desired mode is storage mode, wherein in its storage mode, the deposition openings of the flexible belt overlay on top of the plurality of pill slots of the pill module thereby resulting in the opening the plurality of pill slots to the above for deposition of pills, and the bottom of plurality of pill slots is covered by the flexible belt acting as a floor to each of the plurality of pill slots thereby resulting in the storage of pills that are deposited in each of the plurality of pill slots.

11. The pill dispensing system of claim 8, wherein the desired mode is dispensing mode, wherein in its dispensing mode, a desired dispensing of the flexible belt is displaced underneath a desired pill slot of the plurality of pill slots thereby resulting in the opening at the bottom of the desired pill slot causing any pills held within the pill slots to fall through.

12. The pill dispensing system of claim 1, wherein the communications module communicates with a database that stores a prescription plan for a specific patient to determine a dispensing schedule, wherein the communications module operates the motor to displace the flexible belt in accordance with the dispensing schedule.

13. The pill dispensing system of claim 12, wherein the motor displaces the flexible belt in accordance with the dispensing schedule such that a desired dispensing opening is placed directly beneath a desired pill slot, from the plurality of pill slots, thereby resulting in the pills from the desired pill slot to fall through and make their may their way through the pill dispensing system to a desired pill slot in a pill pack intended for the specific patient.

14. The pill dispensing system of claim 1, wherein the manual fil tray comprises a sensor, wherein the sensor is associated with a specific pill slot in the manual fill tray.

15. The pill dispensing system of claim 1, wherein the manual fill tray comprises a plurality of tension and alignment mechanisms, wherein the tension and alignment mechanisms guide the flexible belt along a path and provide a snug fit between the dispensing belt and the bottom of the slots thereby preventing any pills from escaping the slot from the bottom.

16. The pill dispensing system of claim 1, wherein the manual fill tray comprises a pulley-roller mechanism, wherein the motor rotates the pulley-roller mechanism to displace the dispensing belt in either a clockwise or an anticlockwise direction.

\* \* \* \* \*